United States Patent
Kemper et al.

(10) Patent No.: US 7,536,839 B2
(45) Date of Patent: May 26, 2009

(54) METHOD AND MACHINE FOR CLOSING BOTTLE WITH STERILE CAPS

(75) Inventors: Berthold Kemper, Ahaus (DE); Thomas Niehr, Erkelenz (DE)

(73) Assignee: SIG Technology AG, Neuhausen am Rheinfall (CH)

( * ) Notice: Subject to any disclaimer, the term of this patent is extended or adjusted under 35 U.S.C. 154(b) by 341 days.

(21) Appl. No.: 11/456,096

(22) Filed: Jul. 7, 2006

(65) Prior Publication Data

US 2007/0006550 A1     Jan. 11, 2007

(30) Foreign Application Priority Data

Jul. 8, 2005      (DE) ................. 10 2005 032 322

(51) Int. Cl.
   *B65B 55/04*    (2006.01)
   *B65B 7/28*     (2006.01)
(52) U.S. Cl. ......................... 53/426; 53/478; 53/485; 53/309
(58) Field of Classification Search .......... 53/425, 53/426, 478, 485, 309–312, 317, 331, 331.5
   See application file for complete search history.

(56) References Cited

U.S. PATENT DOCUMENTS

| | | | | |
|---|---|---|---|---|
| 5,857,309 A | * | 1/1999 | Cicha et al. | 53/167 |
| 6,185,910 B1 | * | 2/2001 | Achhammer | 53/426 |
| 6,328,928 B1 | * | 12/2001 | Schroeder et al. | 422/28 |
| 6,341,472 B1 | | 1/2002 | Schroeder | |
| 6,351,924 B1 | * | 3/2002 | Gustafsson et al. | 53/425 |
| 6,457,299 B1 | * | 10/2002 | Schwenke et al. | 53/510 |
| 6,484,477 B1 | * | 11/2002 | Bernhard | 53/426 |
| 2005/0097863 A1 | * | 5/2005 | Taggart | 53/167 |
| 2007/0237672 A1 | * | 10/2007 | Colato et al. | 422/28 |

* cited by examiner

*Primary Examiner*—Hemant M Desai
(74) *Attorney, Agent, or Firm*—Gudrun E. Huckett

(57) ABSTRACT

For closing bottles with sterile caps, the caps are placed in a non-sterile environment in a vertical arrangement and are supplied vertically to a first sterile area. The interior of the caps is arranged to be accessible horizontally. The caps are sterilized in the first sterile area and transferred to a second sterile area where the caps are placed onto bottles. Subsequently, the bottle is closed with the cap. The machine for sterile closing of bottles with caps has a sterilization device with an individualization device for picking up caps and a vertical transport path feeding the caps to the sterilization chamber. A placing device receives the caps from the sterilization device and places the caps onto bottles. A closing device closes the bottles with the cap placed thereon. The sterilization device, the placing device, and the closing device operate as synchronized modules of a linear machine.

37 Claims, 14 Drawing Sheets

METHOD AND MACHINE FOR CLOSING BOTTLE WITH STERILE CAPS

BACKGROUND OF THE INVENTION

The invention relates to a method for closing bottles with sterile caps in which method caps supplied to a transfer device along a transport path are sterilized and subsequently placed onto bottles with their interior facing downwardly.

The invention further relates to a machine for sterile closing of bottles with caps, with which machine the caps are picked up from an individualization device having a transport path, are sterilized in the area of at least one sterile chamber, are placed under sterile conditions onto horizontally supplied bottles, and the bottles are closed by a closing device.

In a method for closing bottles disclosed in U.S. Pat. No. 6,341,472 B1, the caps are supplied along a transport path to a sterile area and subsequently sterilization is realized in a transfer device that is completely arranged within a sterile chamber. The caps picked up individually by means of a rotary machine are pivoted within the sterile chamber so that their interior faces downwardly and placed onto the bottles such that the bottles can be closed subsequently by means of a closure member.

In the field of food product packaging several methods are known in which screw caps after sterilization are picked up by an appropriate screwing device, are moved into the area of the bottle supply, and are screwed onto the bottles.

For sterilizing caps, bottles, containers or similar transport means, methods using hydrogen peroxide are known in order to subsequently fill under aseptic conditions food or the like into containers that have been sterilized externally. Filled bottles are subsequently closed sterilely with an aluminum seal and, outside of the filling machine, the caps are applied in a subsequent method step. Such filling and closing machines are divided with regard to their construction into rotary machines and linear machines that may be provided with a sealing function or a screw-closure function. In the case of a screw-closure function in known machines, the caps are sterilized by means of peracetic acid in a sterilization bath; however, this entails the risk that lubricants contained within the cap are washed out so that later on opening of the bottle is made more difficult. Other methods employ hydrogen peroxide aerosols for sterilization (U.S. Pat. No. 6,341,472 B1) wherein the caps are exposed to a gas atmosphere that is saturated with hydrogen peroxide. These methods are carried out continuously with rotary machines.

SUMMARY OF THE INVENTION

It is an object of the present invention to provide a method and a machine for closing bottles with sterile caps with which method and machine the caps can be manipulated more easily under sterile conditions in a synchronized linear method sequence for vertical lifting movements as well as vertical screwing movements and at increased throughput, wherein at the same time a better protection in regard to recontamination in the area of the caps and the bottles is possible.

In accordance with the present invention, this is achieved in connection with the method in that the caps are sequentially arranged in a non-sterile environment in a vertical row, are supplied into a first sterile area in a substantially vertical advancing direction with their interior being accessible in a horizontal direction, are sterilized in the sterile area, are transferred into a second sterile area, are placed in this area onto bottles that are linearly supplied to this area for forming a bottle-cap unit, respectively, and the bottles are subsequently closed.

In accordance with the present invention this is achieved in connection with the machine in that a sterilization device having a topside individualization device for the caps and receiving the caps via a vertical transport path; a placing device receiving the caps from the exit side of the sterilization device and being connected to a horizontal bottle supply; and a closing device having at least one closing member are configured as modules of a linear machine operating in a synchronized fashion.

In the method according to the invention for closing bottles, the caps are arranged or aligned already outside of a sterilization stretch in such a way that upon subsequent movement of the caps along a vertical guide path a simple loading of a sterilization stretch is achieved. In the area of the sterilization stretch, a sterilization device is provided that can be configured to have a minimal size and that ensures with an overall simple configuration safe protection against recontamination. The intake and exit openings provided for the caps supplied by gravity feed to the short sterilization stretch have advantageously a minimal size. In this connection sterilization air generated by means of an appropriate venting system in the interior of this sterilization stretch is guided with overpressure such that, in addition to providing an efficient flushing cleaning action of the caps, a permanent cleaning effect in regard to the incoming caps as well as in the area of the bottles is effected by means of the outflowing mixture.

The entire closure process is designed such that the aseptic caps are placed onto the bottles by a pick-and-place system so that the bottles are subsequently protected against recontamination and the sealing closure phase with the closure modules providing a recontamination risk has correlated therewith a further sterile area.

Based on this concept of a sterilization device with a vertical transport path, modules of the machine arranged downstream of the sterilization device are arranged such that with these modules a synchronized linear machine is provided. The linear machine is connected in the area of a placing device directly adjoining the sterilization device in a tight space to a horizontal bottle supply. Already in this second sterile area that is kept recontamination-free by means of sterile air, a fluid-tight closure of the bottles can be provided by means of a simple placing member. As an example, a simple snap-on connection between the sterile cap and the supplied bottle is conceivable.

Also, a construction variant of the machine is conceivable in which the cap-bottle unit comprised of the supplied parts is transferred to a downstream third sterile area. In an expedient configuration, the machine concept is designed such that in the area of the placing device the bottles and caps are connected only such that a contamination-tight unit is provided and the unit is finally closed after having been transported to a closing device arranged in a third sterile area, wherein a generally known screw cap or a fused closure or the like can be provided.

Further details and effects can be taken from the following description and the drawings in which a machine according to the invention for performing the method is illustrated.

DESCRIPTION OF THE PREFERRED EMBODIMENTS

Figure 1:
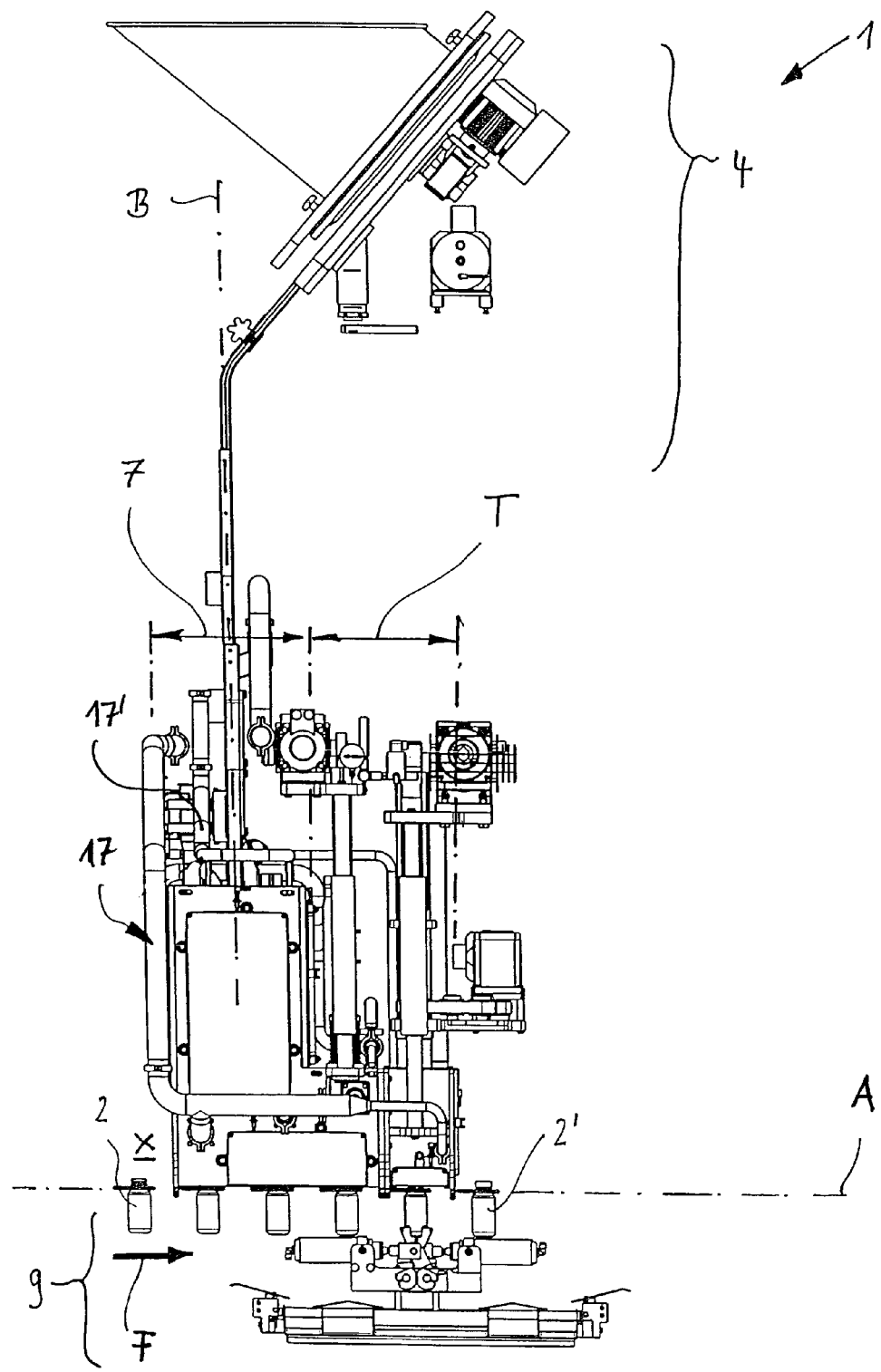
FIG. 1 is a side view of a machine according to the invention as a part of a bottle filling machine not illustrated in detail.

The machine 1 (FIG. 1) for closing bottles 2 with sterile caps 3 employs for the closure process the essentially known cap supply by means of a transport path 5 as a transfer device to a sterile area S from where the caps 3 with downwardly facing interior 18 can be placed onto the bottles 2.

The configuration according to the invention improves such a closure process (FIG. 3) in that the caps 3 are arranged in a vertical arrangement within a non-sterile environment and in this conveying position are supplied, by maintaining the vertical advancing direction (plane B), to the first sterile area S with their interior 18 being accessible in the horizontal direction. After sterilization of the caps 3 in this area S, subsequently a direct transfer into a second sterile area S' is realized in which the placement of the caps 3 onto the bottles 2, linearly supplied into this sterile area S', takes place. Subsequently, the units of bottles and caps formed within the sterile area S', respectively, are either immediately closed or transported away after placement of the caps and are closed in a timely fashion.

The bottle-cap units can be closed immediately in the second sterile area S' by a continued vertical relative movement between cap 3 and bottle 2 to a tight unit or, in a third sterile area S", the tight bottle closure is realized with the cap already placed onto the bottle by means of a screwing movement, a welding (fusing) process or the like. In this way, considered as a whole a linear machine system is provided whose closure process comprises a placement phase and a closure phase. Starting with the transport phase supplying a completely open bottle 2, the placement phase of the cap 3 follows, and only subsequent thereto the phase of the closure process that requires movement-intensive modules takes place. In this way, a spatial equalization, for example, by an additional conveying step, is achieved and under optimal conditions the safety of the aseptic closure process is significantly increased in that recontamination by the moving modules of the caps 3 or the bottles 2 in their open areas is prevented.

In regard to the method, it can be freely selected whether the bottle closure is realized by a relative movement between the cap 3 and the bottle 2 employing a push-and-snap-on process or whether the bottle and the cap are connected to one another by a screwing process, a welding process or the like.

The closure caps 3 that are sorted outside of the first sterile area S with horizontally aligned interior 18 into respective vertical areas (plane B) of transport paths 5 are further transported in a synchronized fashion within a first sterile area S that is to be passed in a vertical direction; subsequently, sterilization, in particular, with hydrogen peroxide, takes place in a horizontal spraying direction C. Subsequently, the caps 3 are transported on a transport stretch L, defining the residence time for sterilization, to a spraying or flushing area and a drying area; in an advantageous embodiment, the caps 3 are deflected directly on the transport path 5 into a position with downwardly facing interior 18. In this position, the caps 3 reach the second sterile area S' and are placed here onto the bottles 2.

The machine 1 is designed in the area of the sterilization device 7 such that already during the vertical supply phase of the caps 3 a presterilization on their exterior side and interior side is achieved; in this connection, an air-sterilization agent mixture 25 flowing out of the first sterile area S is efficiently used. By an appropriate contouring in the area of the transport path 5 it is ensured that already in this supply phase the interior 18 of the caps 3 can also be sprayed.

For the spraying or flushing treatment of the caps 3 upon passing the first sterile area S, the sterilization agent that is supplied at least phase-wise is introduced with overpressure into the interior 18 of the caps 3 and, after a substantially variably adjustable residence time that is defined by the indexing of the system and the spacing of the spraying and drying areas, drying is carried out by blowing out the interior 18 of the caps 3.

By appropriate dimensioning of the transport stretch L in the area of the transport path 5 a method control is possible in which in a first sterile area at the same time several of the caps 3 supplied on the transport path 5 are sterilized with overpressure so that accordingly to the cycle control within the spraying area for example three spraying cycles have to be passed and, subsequently, also a multi-phase drying area is passed.

Figure 6:
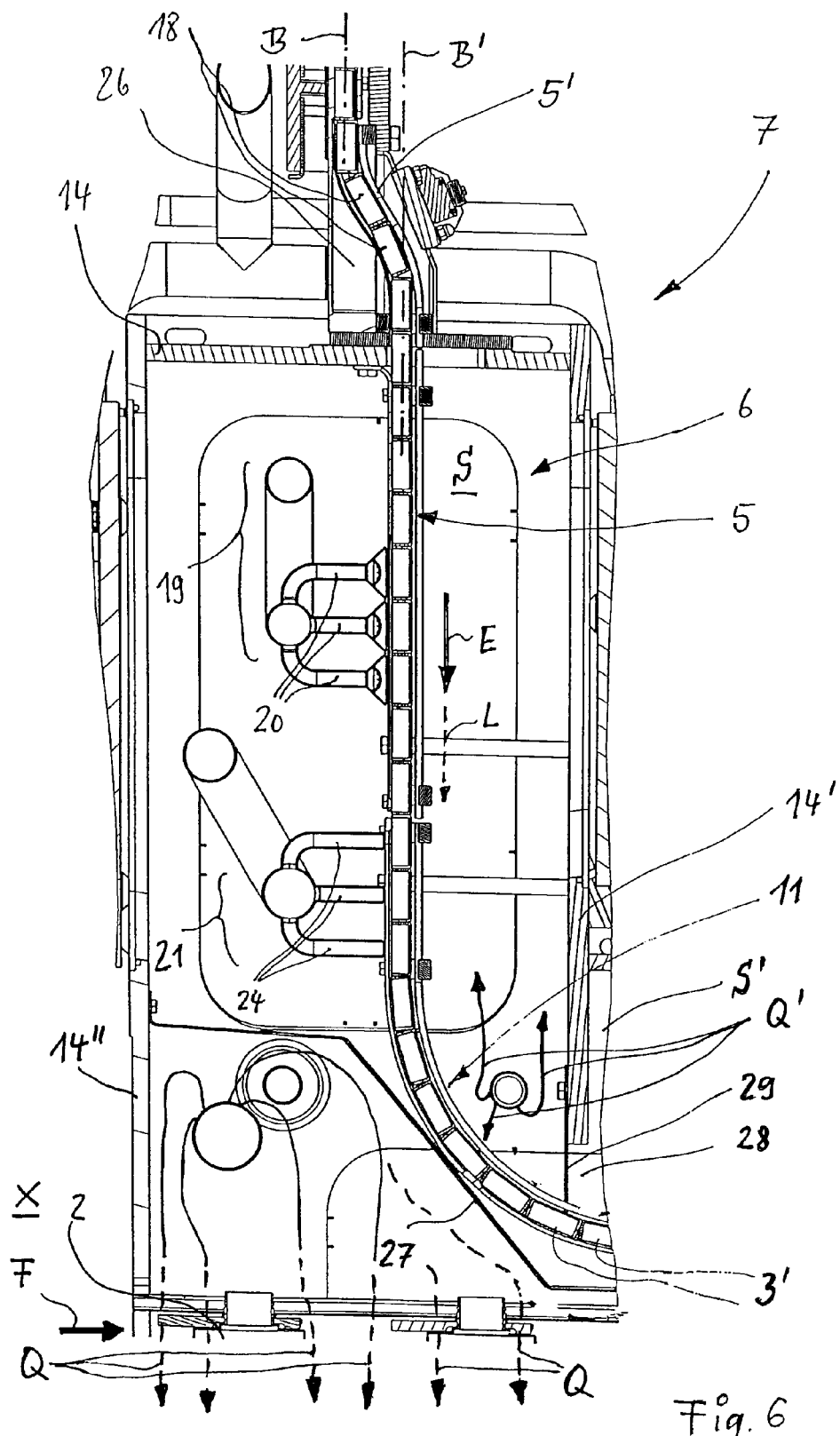
FIG. 6 is a detail illustration of the machine in the area of a device for sterilizing the supplied caps.

The linear machine 1 that as a whole has a compact serial arrangement of its modules enables optimal control of the sterile air required for the method wherein an efficient recontamination protection is achieved by its optimal utilization. In this connection it is provided that the vertical first sterile area S, the second sterile area S' defining the placing area, and the third sterile area S" provided especially for screwing on the caps 3 are protected from recontamination by individually generated displacement flows containing sterile air and/or sterilization agent. In FIG. 6 (flows according to arrow Q and Q'), FIG. 7 (flows according to arrow G, G', G"), FIG. 11

Figure 17:
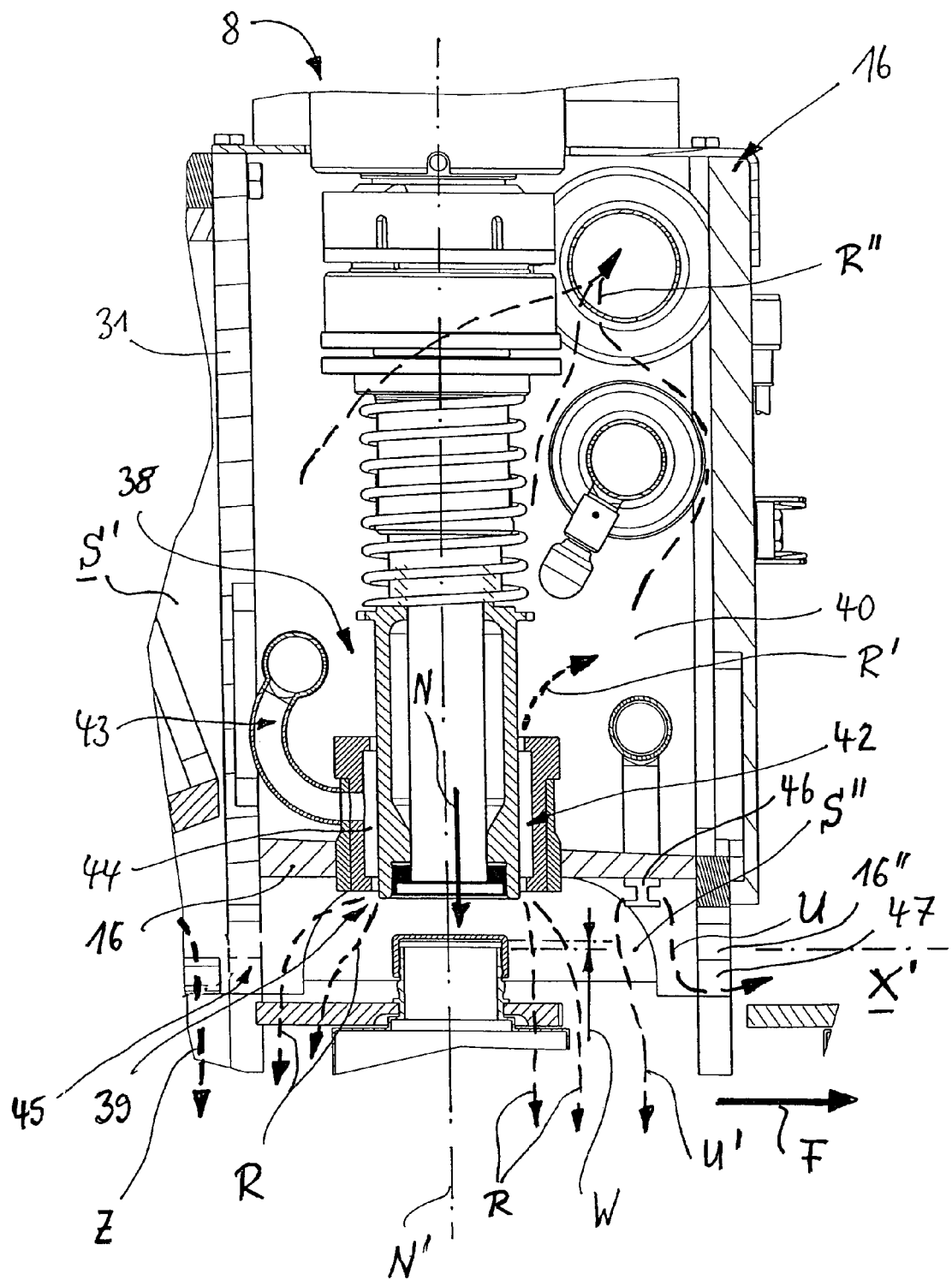
FIG. 17 is a detail illustration of a third sterile area having a screwing device.

(flows according to arrow Z), and FIG. 17 (flows according to arrows R, R' and U, U'), these conditions are exemplified. Important in this connection is that in a zone between first and second sterile areas S, S' there are displacement flows, respectively, for preventing recontamination of the caps 3 as well as the supplied and already filled bottles 2, for example, by means of sterile air (flows Q and Z). In this way, already upon placing the caps 3 on the bottles 2 an aseptic closure of the bottles 2 is ensured.

In the inventive method it is provided that at least in the area where the caps 3 are placed onto the bottles 2 a sterile air supply is realized and, from it, a diversion (arrow Z) across the bottles 2 arriving in the horizontal supply plane A is realized. It is also conceivable that a diversion (arrow Q') is provided in the higher first sterile area S. In an advantageous configuration of the flow guiding action, laminar flow is generated and in the area between the closure phases a vertical diversion without transverse flows or turbulences is effective.

It is understood that the method, essentially explained based on a supply path B or a supply plane A, and the accordingly designed machine 1 have a multi-path arrangement of the device modules. In particular it is provided that the plastic bottles 2 and the caps 3 are combined by means of an eight path supply (FIG. 2) in a synchronized fashion into the second sterile area S'' and from here are transported away as a bottle-cap unit for undergoing the final closure action.

In FIG. 1, a machine identified as a whole by reference numeral 1 is illustrated as a part of a linear filler, not illustrated in detail, for sterile closing of bottles 2 with caps 3. In this connection, it is apparent that the caps 3, starting at an individualization device 4 as it is known in the art, are sterilized on a transport path identified at 5 in a sterilization device 7 having a sterilization chamber 6, are placed under sterile conditions onto bottles 2 that are supplied in a horizontal supply plane A, and, subsequently, the bottles 2 are closed by a closing device 8.

In the concept of the machine 1 according to the invention, it is provided that a topside individualization device 4 is connected by a transport path 5 defining a vertical plane B to the sterilization device 7. The sterilization device 7 interacts with a placing and/or closing unit T that receives the caps 3 from the exit side of the sterilization device 7 and is connected to a horizontal bottle supply 9. These modules 4, 7 as well as T together with a closing device 8 having at least one closing member 10 form a synchronized aggregate in the form of a linear machine (FIG. 3).

Figure 2:
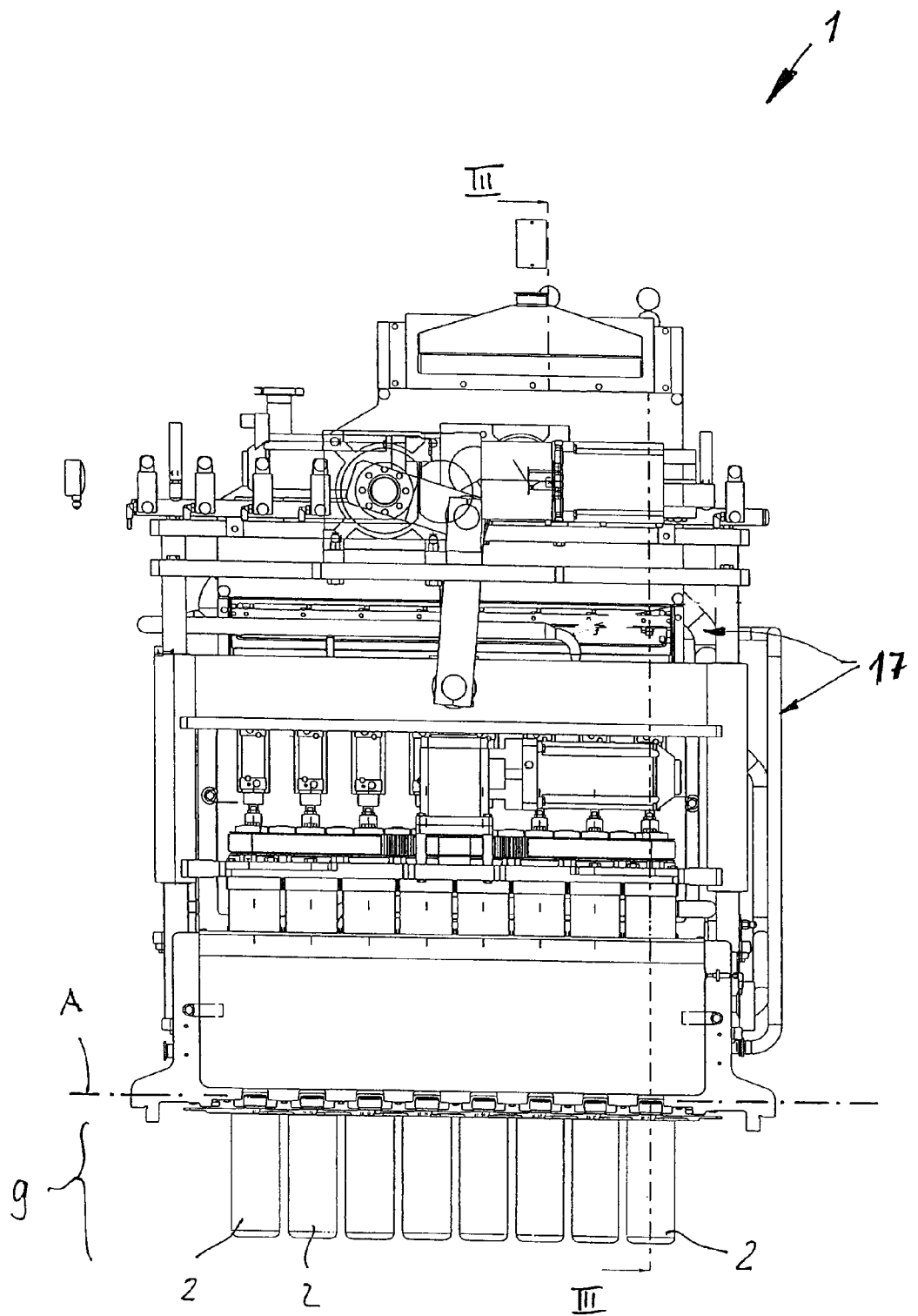
FIG. 2 is a front view of the machine according to FIG. 1.
Figure 3:
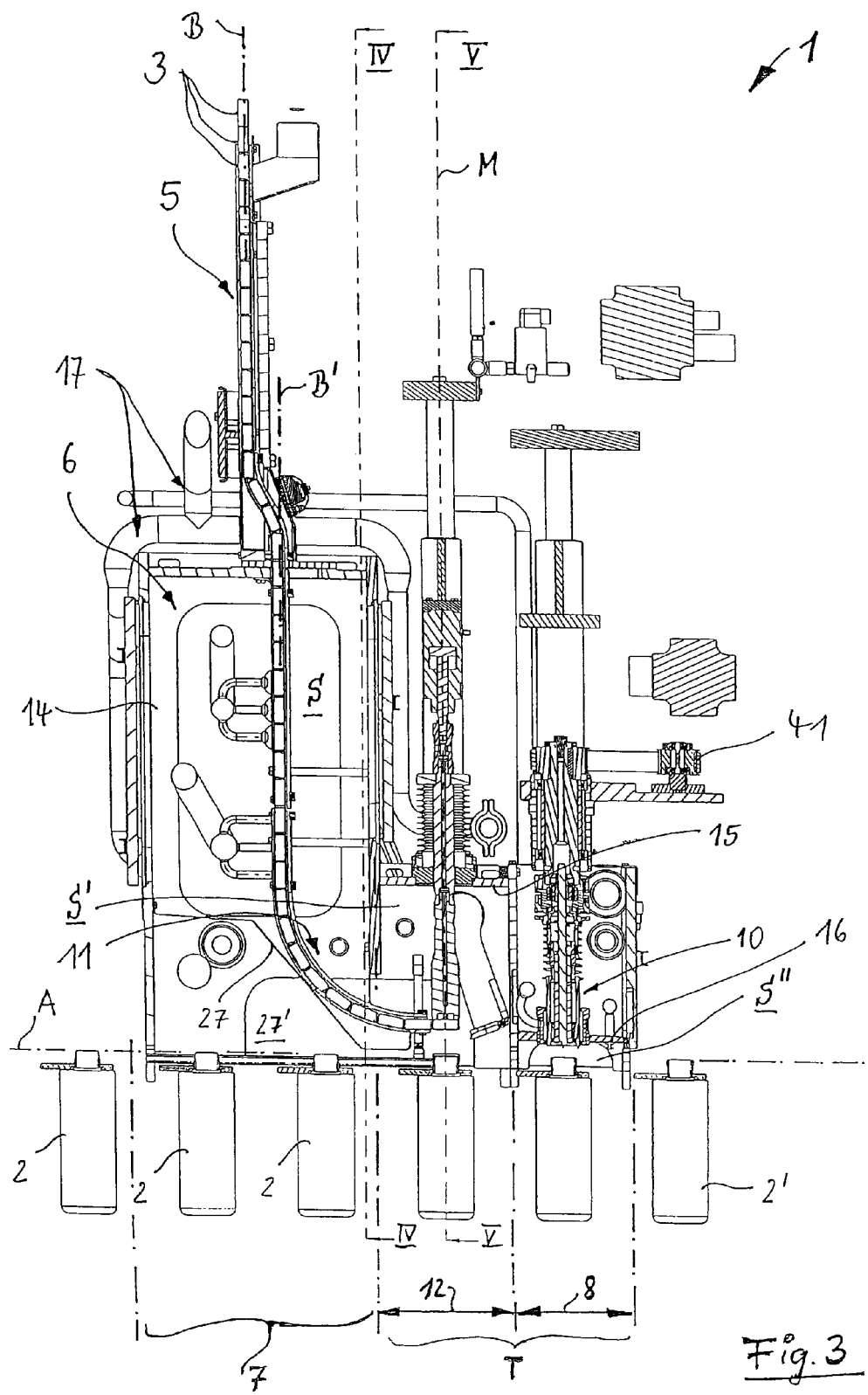
FIG. 3 is a section view of the machine according to section line III-III in FIG. 2.
Figure 4:
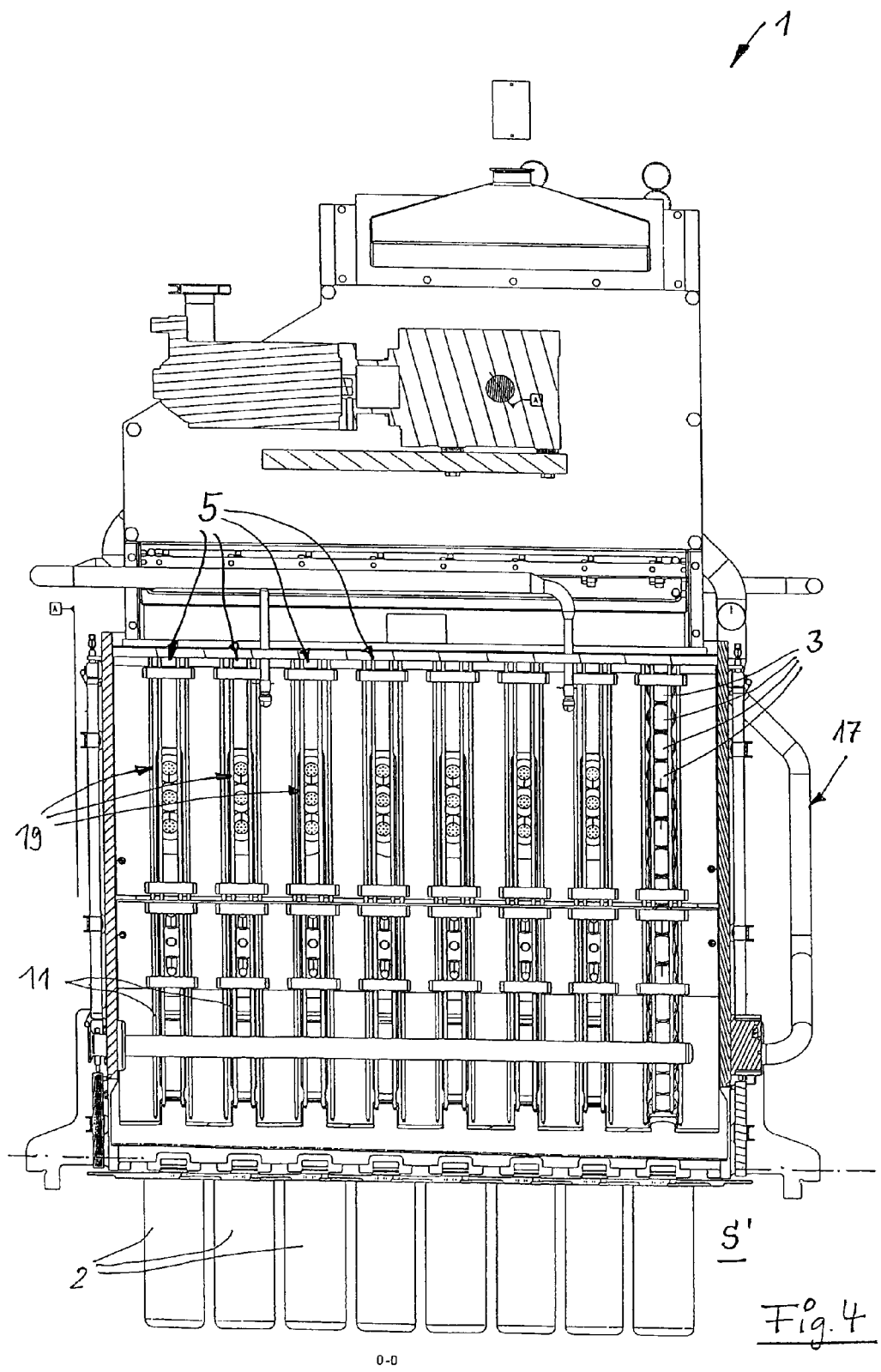
FIG. 4 is a sectioned front view of the machine according to section line IV-IV in FIG. 3.
Figure 5:
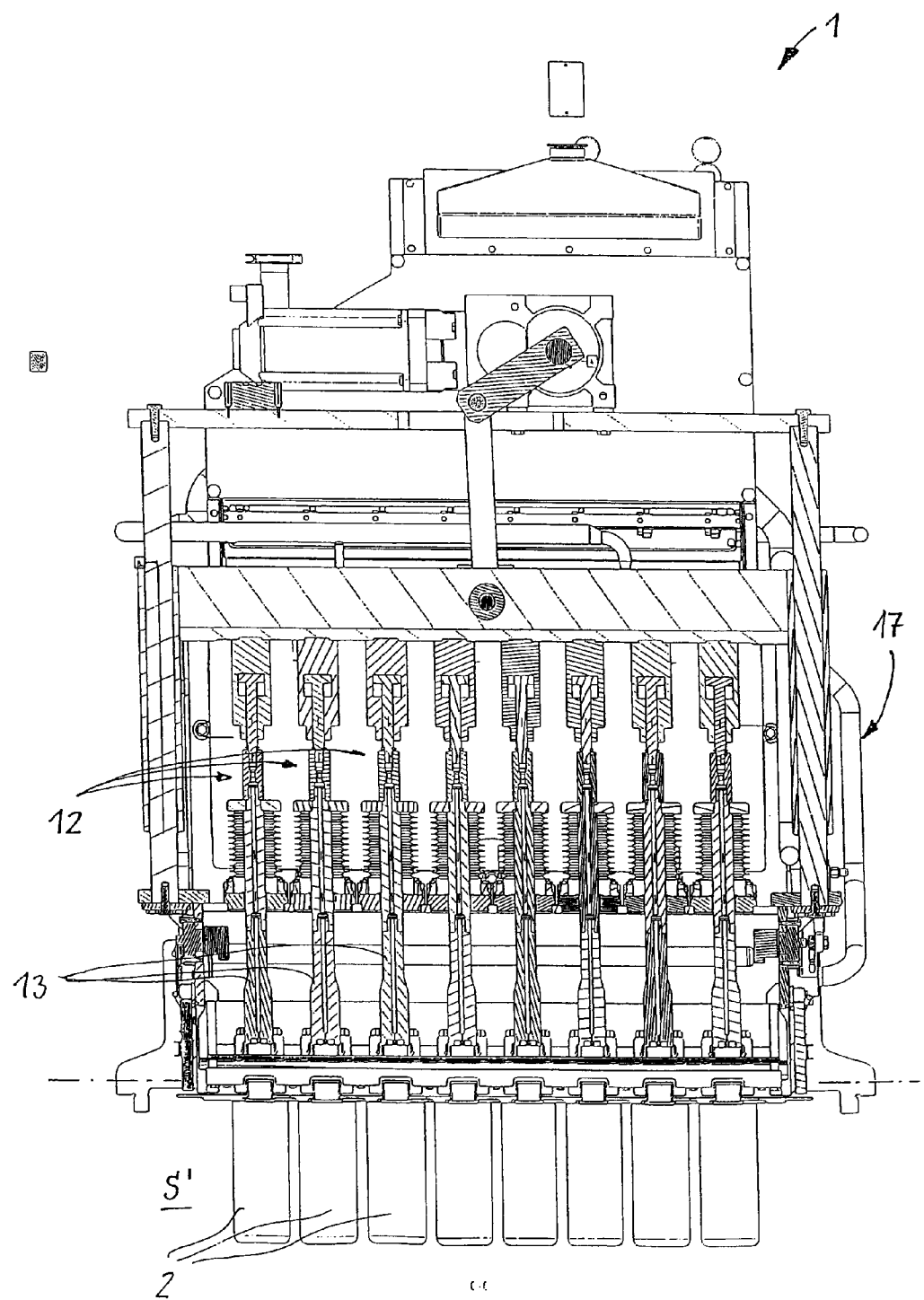
FIG. 5 is a section illustration similar to FIG. 4 according to section line V-V of FIG. 3.

In the illustrations according to FIGS. 2 to 5, different views show the principal configuration of this linear machine 1 that realizes, particularly for a hydrogen peroxide sterilization, parallel closing processes in a multi-path, preferably eight path, configuration (FIGS. 2, 4, 5). In a unit that is advantageously of a compact design with reduced technical expenditure, improved hygiene is achieved by a two-step closure process carried out in separate sterile housings.

Figure 7:
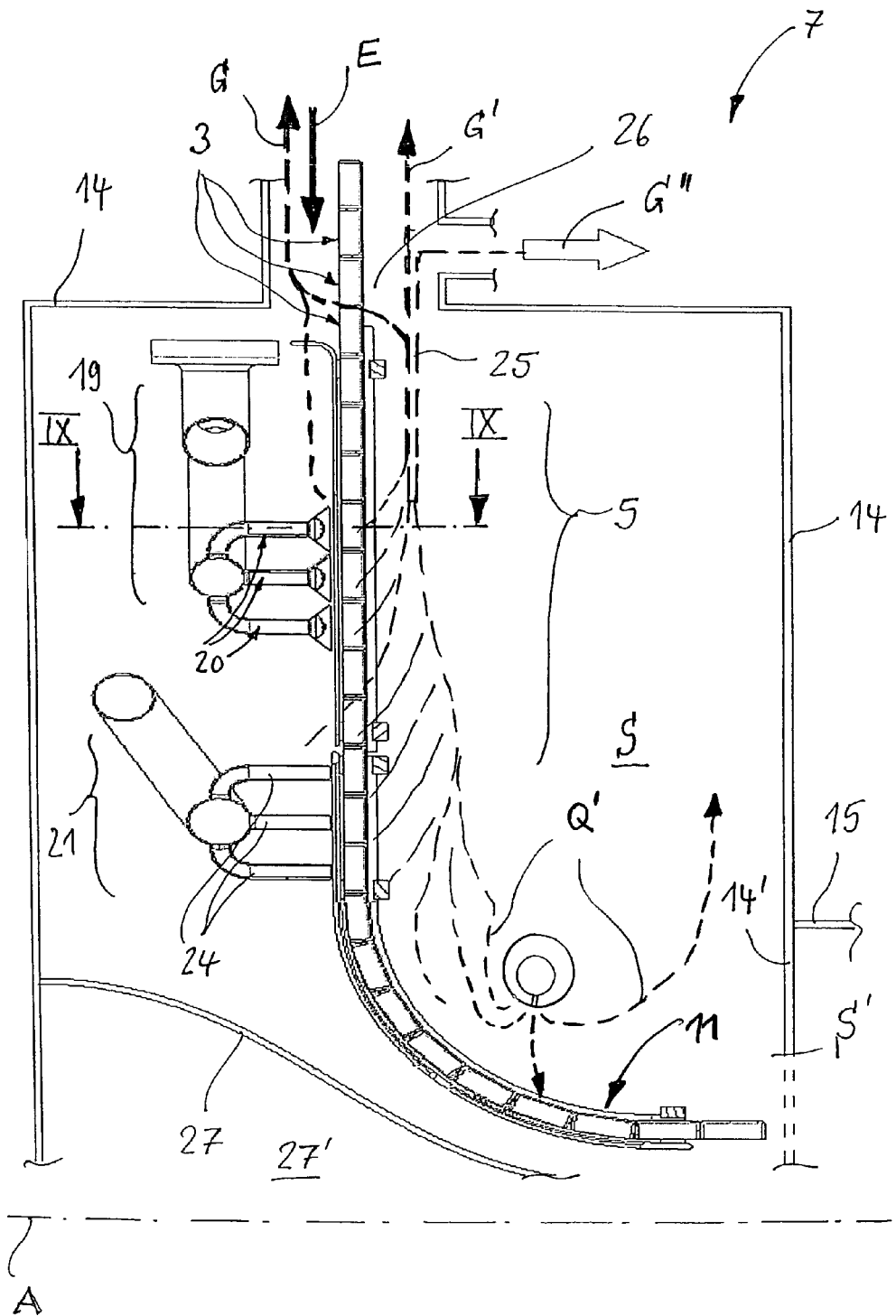
FIG. 7 is a principal detail illustration of the sterilization device according to FIG. 6.

The section illustration according to FIG. 3 shows in connection with FIG. 6 and FIG. 7 the displacement phases when supplying the caps 3, wherein the caps are supplied on the transport path 5 vertically through the sterilization device with sterile chamber 6 (FIG. 3) identified as a whole as partial area 7 in which a first sterile area S is provided. At the lower end of the transport path 5 a deflection section 11 of the path 5 is provided that has an outlet proximal to the placing device 12 arranged in the second sterile area S'. This placing device 12 has a placing member 13 (FIGS. 10 through 16) that can be embodied in the linear machine 1 of the present invention for placing the cap on the bottle as well as closing the bottle with the cap. Instead of the deflection section 11 that conveys the caps 3 by gravity feed it is also conceivable to provide a pivot mechanism or similar conveying elements (not illustrated) that transfer the caps 3 into the sterile area S'.

Directly downstream of the second sterile area S', a third sterile area S'' comprising the closing device 8 with closing member 10 is provided wherein the sterilization device 7, the placing device 12, and the closing device 8 are arranged in the sterile housings 14, 15, 16, respectively, illustrated in the section illustration of FIG. 3. These modules are advantageously positioned above the bottle conveying part of the bottle supply 9 supplying the bottles 2 horizontally in such a way that a direct serial arrangement of the sterile areas S, S', S'' (FIG. 3) is provided. It is also conceivable that these sterile areas are arranged spaced from one another in the supply direction F at a spacing that defines an idle cycle (not illustrated).

The general views of the machine 1 according to FIGS. 1 and 2 show that a venting system referenced by numeral 17 opens in the respective sterile housings 14, 15, 16; the venting system 17 cooperates with nozzles arranged in the sterile areas S, S', S'' and described in the following in more detail in regard to their control and distribution functions. This venting system 17 that ensures the sterile closure process and the distribution of supply and exhaust air is designed such, in particular after automatic cleaning of all modules of the machine 1, that also their sterilization can be performed with minimal expenditure. For this purpose, additional cleaning lines 17' (FIG. 1) are provided that are not disclosed in detail in this context.

Figure 9:
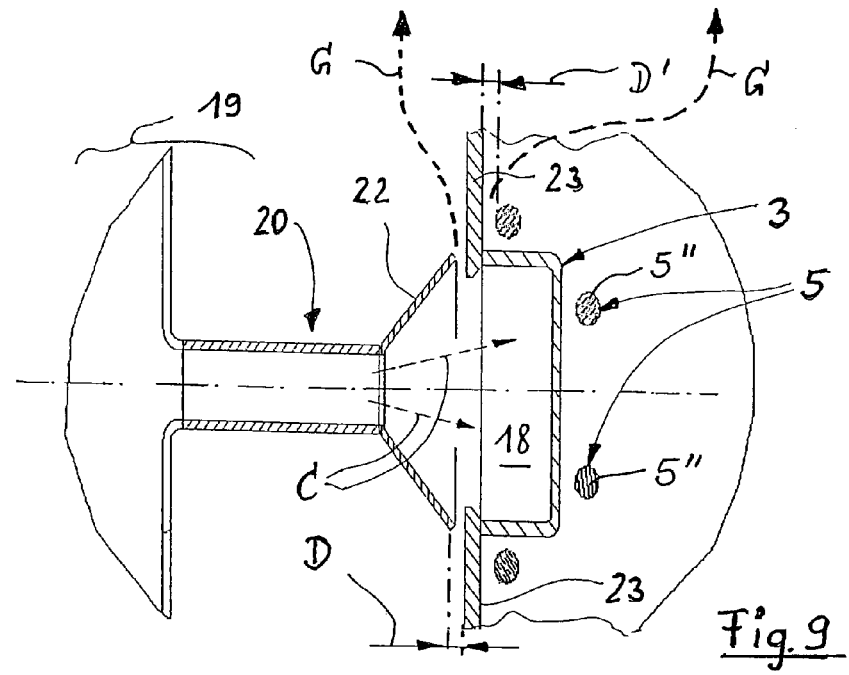
FIG. 9 is a section illustration of the sterilization device according to a section line IX-IX of FIG. 7.

The detail illustration according to FIGS. 6 and 7 show that the sterilization device 7 in the proximal area of the caps 3 supplied vertically on the transport path 5 (supply plane B') has an aerosol flushing module 19 supplying a sterilization agent; the module 19 has several spray nozzles 20. The caps 3 are supplied by means of the device 4 such onto the transport path 5 that the caps 3 in the upper area of the path 5 are facing the spray nozzles 20 with their substantially horizontally accessible interior 18 (FIG. 9).

Downstream of this module 19 a drying module 21 with several drying nozzles 24 for flushing the caps 3 with hot and/or cold air is arranged (FIG. 6, FIG. 7). Downward of this module 21, an arc-shaped deflection section 11 of the transport path 5 is provided that opens therefore at the bottom side of the sterile housing 14 and the sterile area S of the sterilization device 7 so that the sterilized caps 3' are transferred along an advantageously short stretch into the second sterile area S'.

The aerosol spraying module 19 (FIG. 9) has in the area of the spraying nozzles 20 a cover part 22, respectively, that widens in a cone shape toward the caps 3 located on the transport path 5. In the area of the cover part 22 the interior 18 of the cap 3 facing in the closed position (FIG. 10) the product in the bottle 2 is directly sprayed with the aerosol (FIG. 9, arrow C), for example, with a 33% hydrogen peroxide solution. The construction is such that between the conical cover part 22 and the transport path 5 or the sidewalls 23 connected thereto a minimal gap D is formed and the flushing action carried out with overpressure in the interior 18 of the caps 3 is therefore possible with increased efficiency. The side views according to FIG. 6 and FIG. 7 show in this connection that in the area of the flushing module 19 several parallel spray nozzles 20 are provided that are arranged above one another. Under the effect of the spray pressure C the cap can be moved toward the guide parts 5'' of the path 5 so that a gap D' is formed for exhausting the hydrogen peroxide.

Downward of the three aerosol spray nozzles 20 in the advancing direction E of the caps 3, drying nozzles 24 of the drying module 21 are provided, respectively. For a uniform synchronized advancing action of the caps 3 this module 21 also has three drying nozzles 24 wherein between the modules 19 and 21 two idle cycles are provided in the illustrated configuration (arrow L, FIG. 6) so that in this way a transport stretch that defines an effective residence time for the hydrogen peroxide aerosol is provided; based on the number of the idle cycles, the residence time is variably adjustable.

In the principal illustration according to FIG. 7 the sterilization device 7 with sterilization housing 14 is illustrated in more detail. It is shown in particular that the exhaust air 25 exiting from the sterile area S or the modules 19 and 21 is mixable with the hydrogen peroxide aerosol of the flushing module 19 and this aerosol-air mixture (dashed lines in FIG. 7) can be diverted counter to the supply direction E of the caps 3 in a flow direction G, G' through a passage 26 out of the sterile housing 14 toward the top side individualization device 4. In this way, the caps 3 are substantially completely flushed and are thus advantageously exposed to a pretreatment (pre-sterilization). By means of an upper deflection area 5' (FIG. 6) in the proximity of the passage 26 the caps 3 are oriented such that the flow G also accesses the interior 18.

Figure 8:
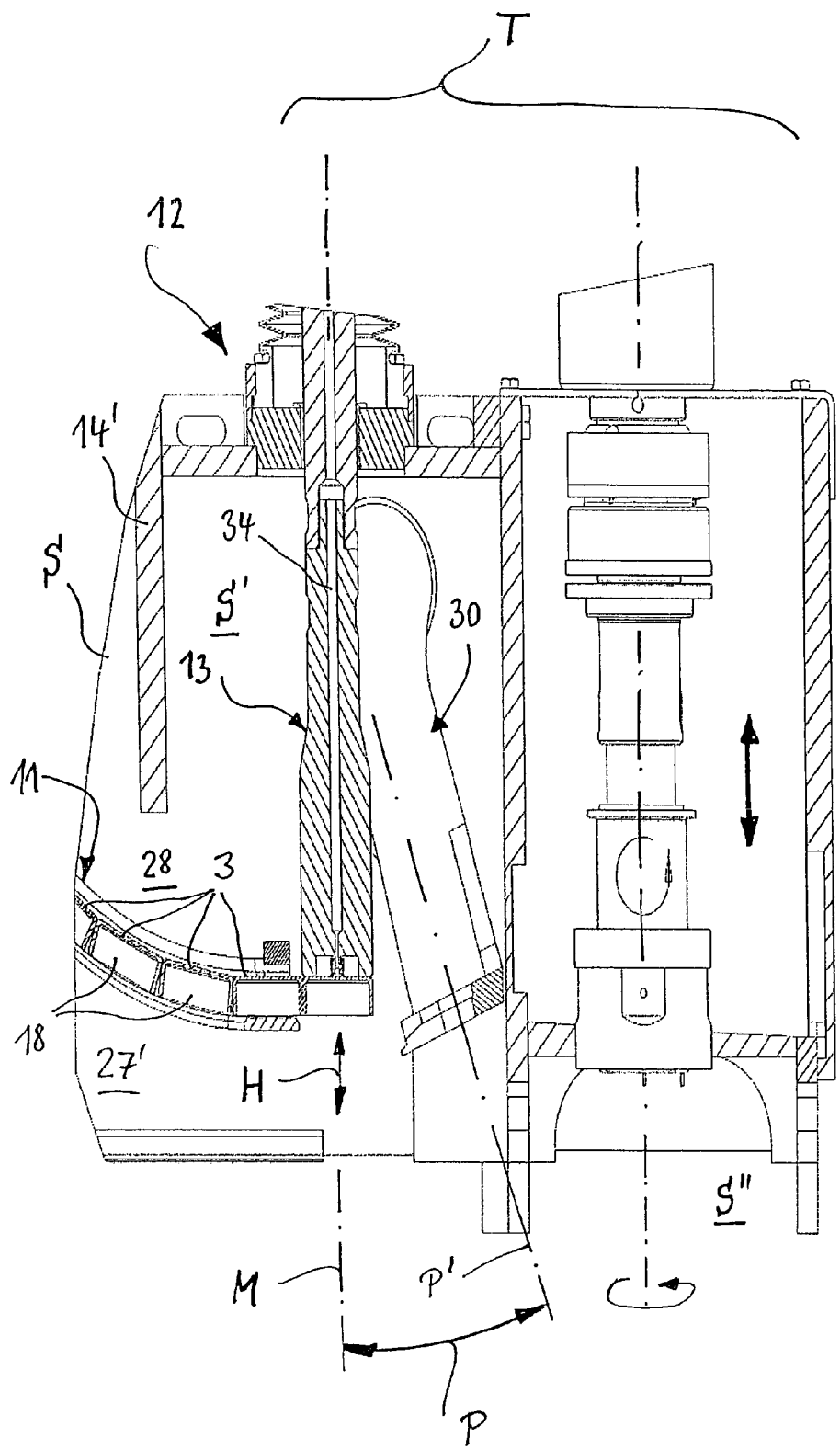
FIG. 8 is an enlarged detail view of the lower end area of the sterilization device at a transition to the second sterile area.
Figure 10:
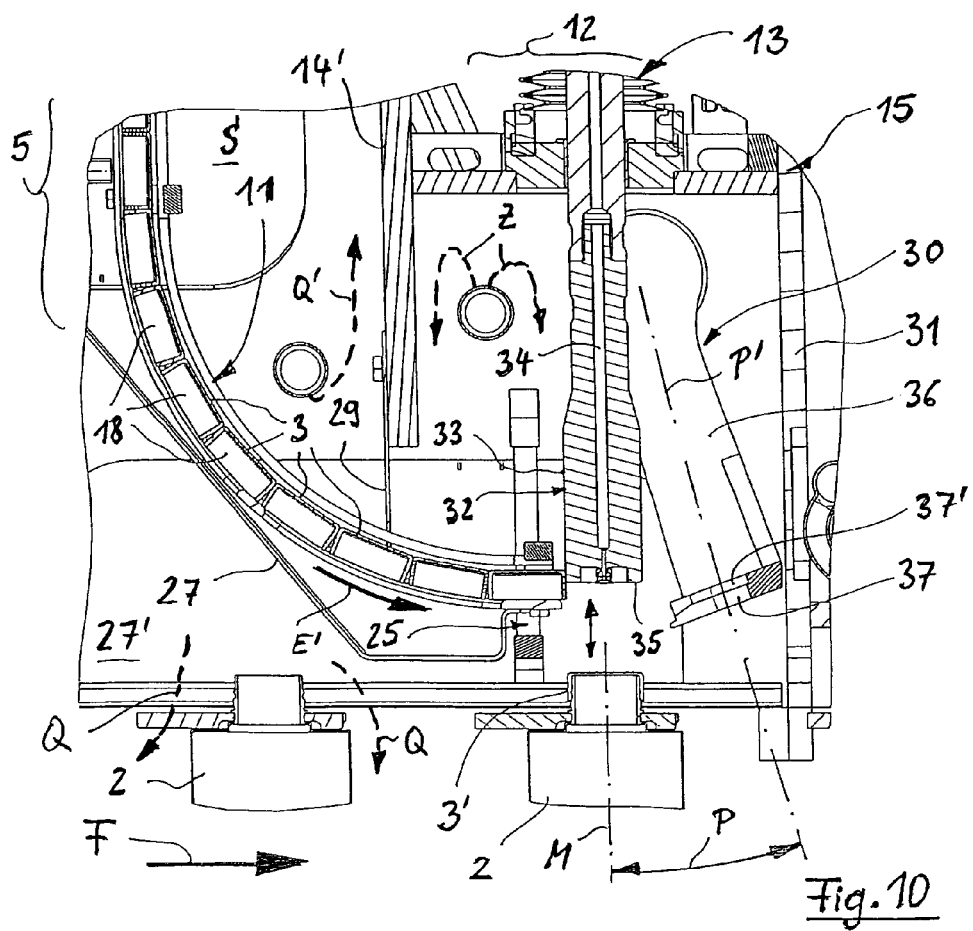
FIG. 10 is a detail illustration of the second sterile area showing a first phase of the transfer of a sterile cap to the placing device.

FIGS. 6 and 7 show clearly that the sterilization device 7 in the proximal area of the lower deflection section 11 of the transport path 5 has a separating wall or partition 27 that extends into the second sterile area S' of the placing device 12 and substantially horizontally across the bottle supply 9. Above this partition 27 the deflection section 11 opens through an opening 28 (FIG. 8) provided in the housing wall 14' and acting as an air passage into the second sterile area S'. The size of this opening 28 is variable with regard to its opening cross-section by means of an adjustable closure flap 29 (FIG. 6). FIG. 10 shows this transfer area; it is apparent that the lower partition 27 is a shield relative to the area of the upwardly open bottles 2 (conveying direction F). The front end of the partition 27 is secured on a support 25 that engages the end of the transport path 5; the support, in turn, defines a passage between the sterile area S'' and the partition chamber 27'. In FIG. 6, the flow arrows Q indicate the laminar distribution wherein in the area of the front wall 14'' the filled bottles 2 coming in from the upstream filling zone X are protected immediately by a sterile air jet against recontamination.

The enlarged detailed illustrations according to FIG. 8 and FIGS. 10 to 16 show an embodiment of the placing device 12 provided in the second sterile area S' which together with the screwing device 8 forms the module T. The vertically movable placing member 13 (movement arrow H, FIG. 8) of the device 12 inter acts in different phases with a pendulum holder 30 that engages the caps 3 supplied by the deflection section 11 in such a way that the caps 3 in a first movement phase are gripped and simultaneously individualized.

Figure 11:
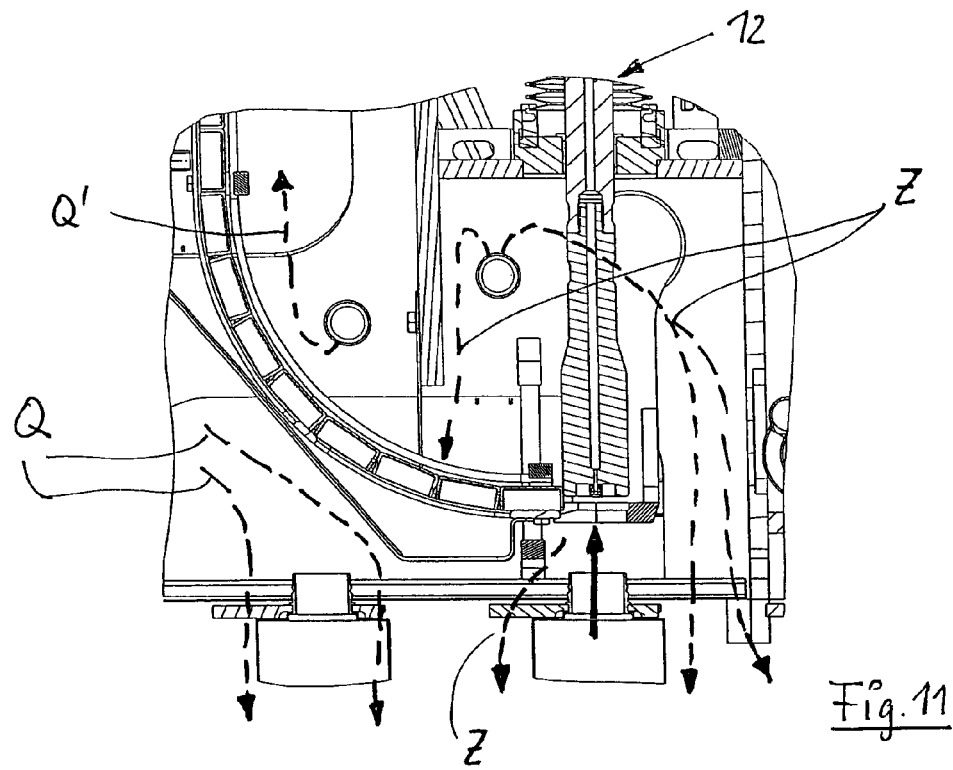
FIG. 11 is a detail illustration of the second sterile area showing a second phase of the transfer of the sterile cap to the placing device.

The pendulum holder 30 is movable between the placing member 13 having a vertical longitudinal center plane M and a second vertical wall 31 of the housing part 15 defining the second sterile area S' at the exit side wherein a pivot movement (arrow P) in or counter to the bottle conveying direction F is carried out such that the pendulum axis P' is pivoted away from its congruent position with the vertical axis M of the device 12 (FIG. 10) and returned (FIG. 11).

Figure 16:
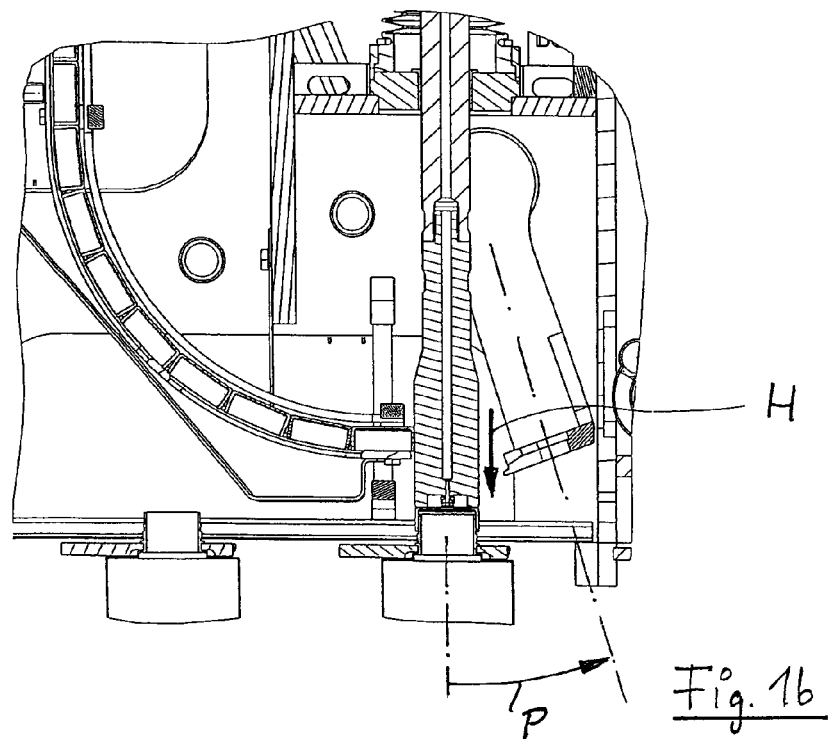
FIG. 16 is a detail illustration of the second sterile area showing a seventh phase of the transfer of the sterile cap to the placing device.

The placing member 13 has a forward cylinder part 32 that with its outer side 33 can be moved vertically in front of the opening of the deflection section 11 supplying the caps 3 (FIG. 10). When looking at the row of sterilized caps 3 provided in the deflection section 11, the leading cap 3, respectively, can be transported individually in the arc-shaped advancing direction E' when the pendulum holder 30 is in an upper release position illustrated in FIG. 12. Based on this phase according to FIG. 13, the placing device 12 is controllable in principle such that the gravity-fed cap 3 is engaged by the placing member 13; upon subsequent vertical lowering movement (arrow H, FIG. 8) of the placing member 13 the cap 3 is placed onto the bottle 2; and simultaneously the next cap 3 in the area of the deflection section 11 can be retained by means of the outer side 33 of the cylinder part 32 (FIG. 16).

Figure 12:
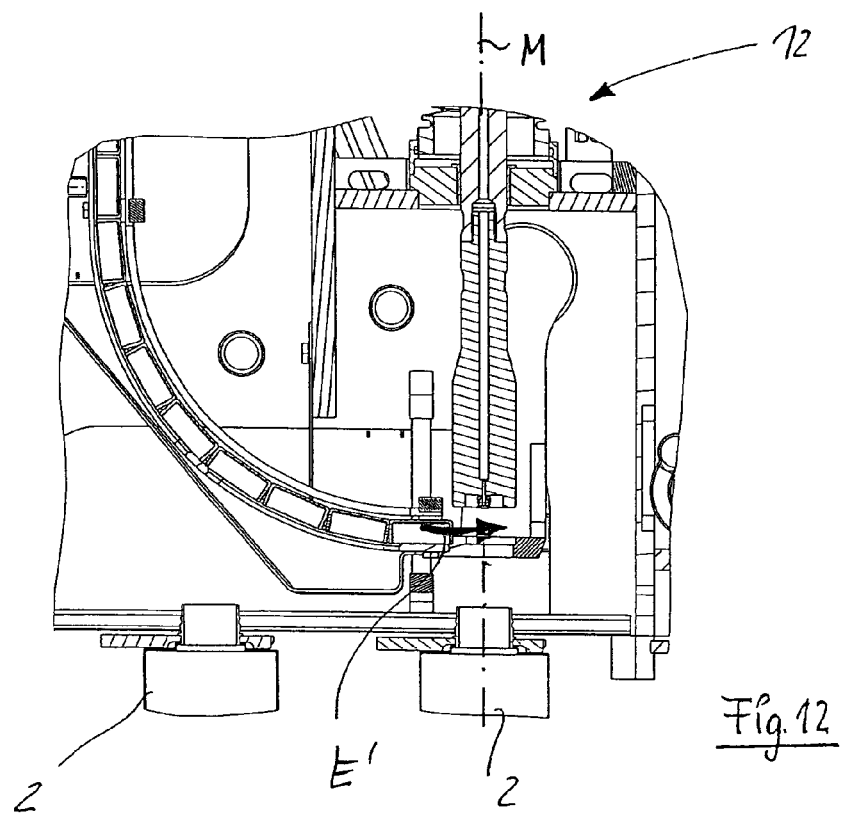
FIG. 12 is a detail illustration of the second sterile area showing a third phase of the transfer of the sterile cap to the placing device.
Figure 13:
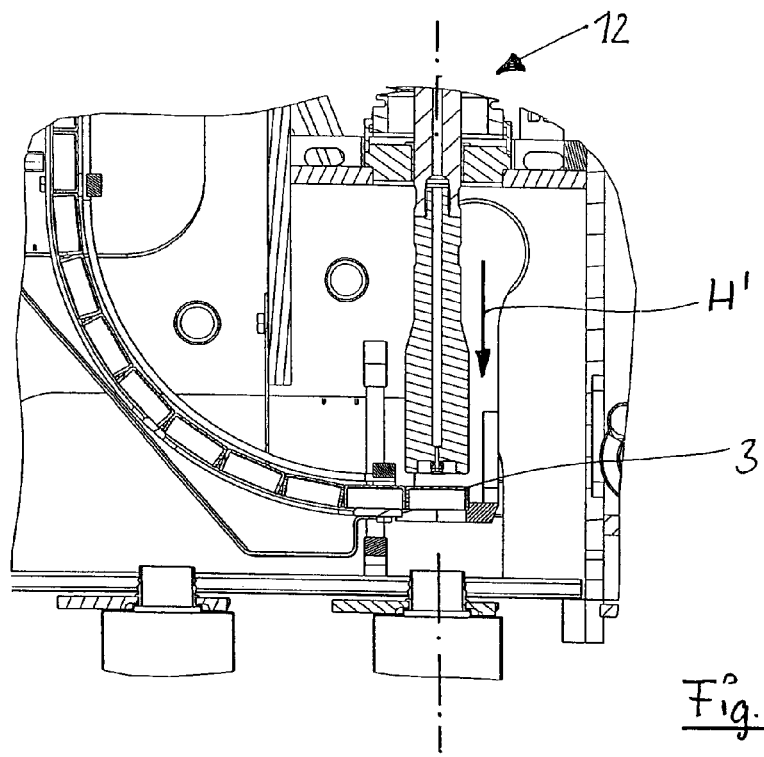
FIG. 13 is a detail illustration of the second sterile area showing a fourth phase of the transfer of the sterile cap to the placing device.
Figure 14:
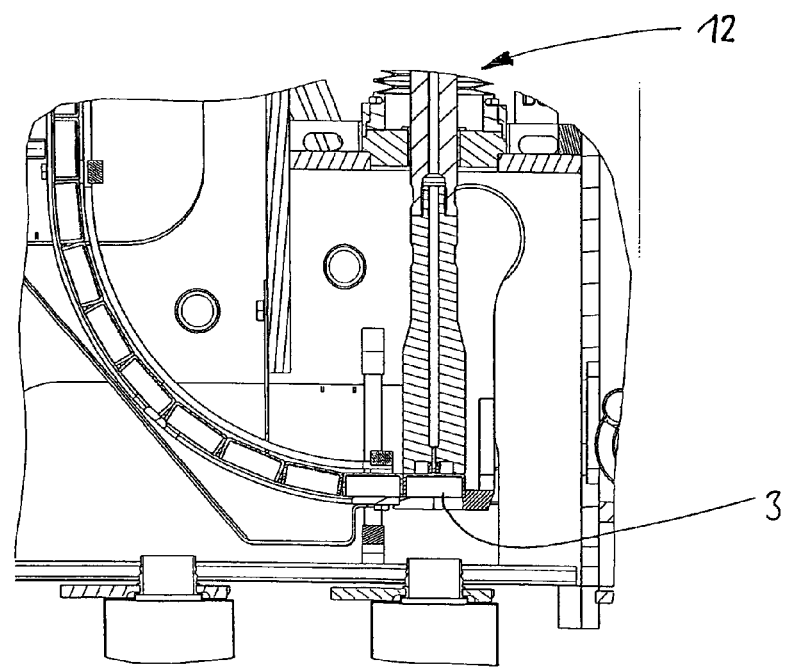
FIG. 14 is a detail illustration of the second sterile area showing a fifth phase of the transfer of the sterile cap to the placing device.
Figure 15:
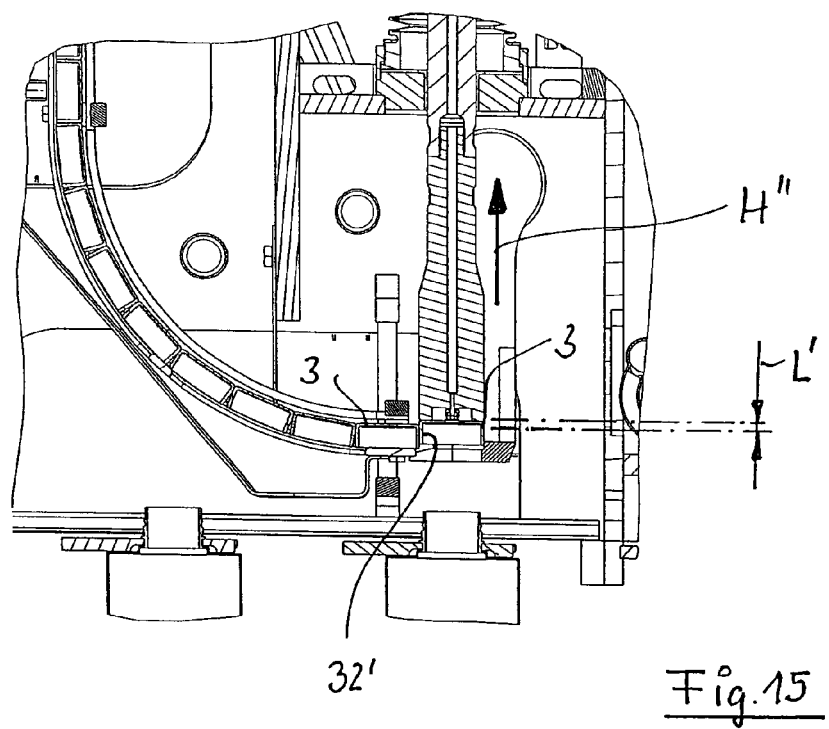
FIG. 15 is a detail illustration of the second sterile area showing a sixth phase of the transfer of the sterile cap to the placing device.

This manipulation system has a placing member 13 that is provided in the area of the cylinder part 32 with a bore 34 to be supplied with suction air; the bore 34 opens at the end face in the area of an annular surface 35 of the cylinder part 32. It is also conceivable to use in place of the cylinder part 32 a conical configuration of this part 32 (not illustrated). According to FIGS. 13 to 15 the suction phase for picking up the cap 3 supplied to the pendulum holder 30 is shown wherein in this phase the placing member 13 is lowered by stroke H' (FIG. 13) and the cap 3 is engaged in a suction position according to FIG. 14. Up to this point, the cap 3, based on the advancing phase E' according to FIG. 12, is secured in an L-shaped receiving arm 36 of the pendulum holder 30 (FIG. 14). The receiving arm 36 has for this purpose a short leg 37 with a receiving contour 37'.

After placement of the placing member 13 onto the cap 3 (FIG. 14), the cap 3 is lifted by a short stroke L' (stroke movement H'', FIG. 15) and, at the same time, the next cap 3 within the deflection section 11 of the path 5 coming from the sterile area S is retained by the cylinder part 32' of the lifted cap 3. In this lifted position H'' according to FIG. 15 the L-shaped receiving arm 36 of the pendulum holder 30 is pivoted in the direction of arrow P away from the area of the placing member 13 so that in the direction of the vertical axis M the opening of the bottle 2 is accessible and now the cap 3 held by vacuum can be vertically downwardly moved toward the bottle 2 (arrow H, FIG. 16).

In accordance with a closing position of the cap 3 selectable within the system, the bottle 2 is already at this point tightly closed (not illustrated). In accordance with the cap-bottle unit the placing member 13 is adjustable in the direction toward the bottle 2 to a corresponding length of the vertical stroke movement H. In the machine 1 the cap 3 is pushed only into a contact position as shown in FIG. 17 and, in a subsequent phase, is securely and fluid-tightly closed.

Figure 18:
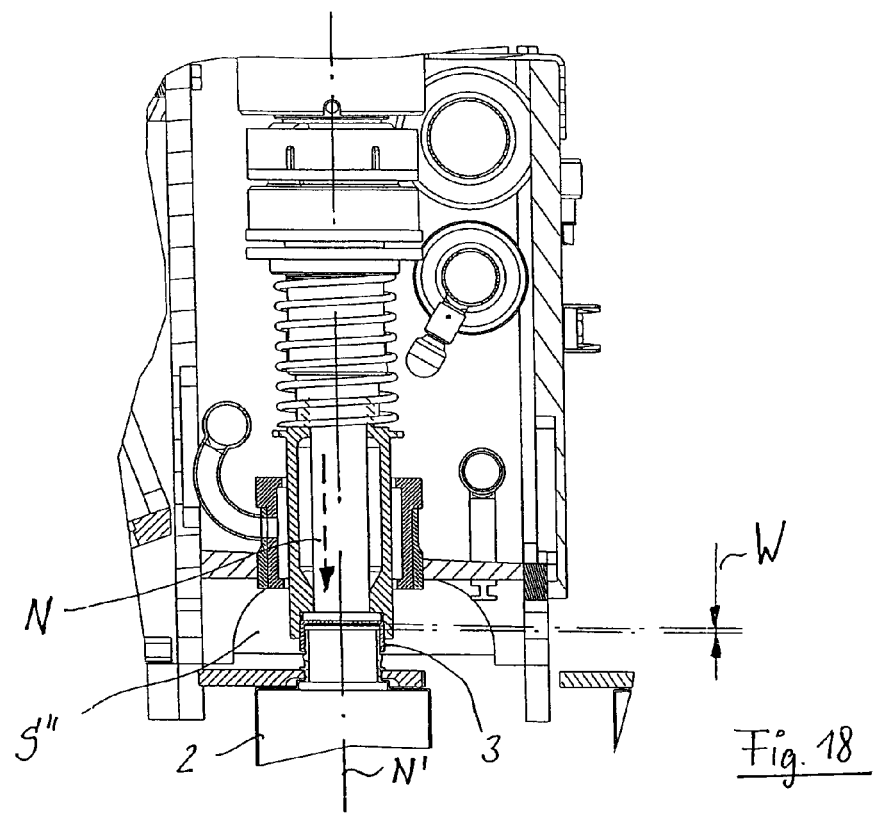
FIG. 18 shows a first movement phase of the screwing device for screwing the cap onto the bottle.
Figure 19:
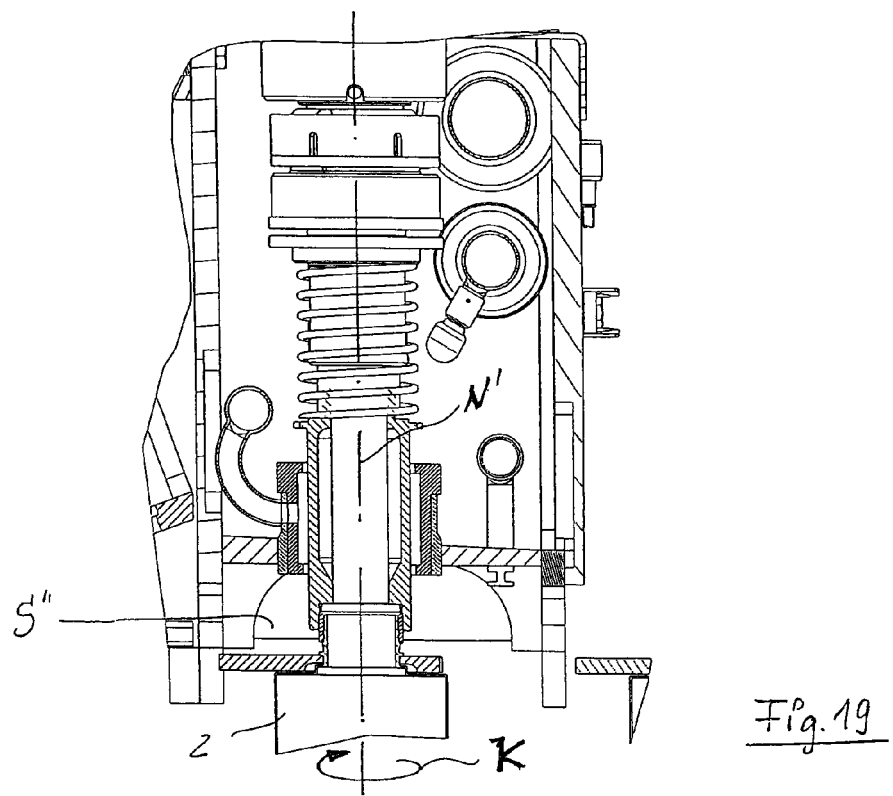
FIG. 19 shows a second movement phase of the screwing device for screwing the cap onto the bottle.

In FIGS. 17 through 19, the closing device 8 configured as a screwing module and provided in the third sterile area S''' of the synchronized linear machine 1 is illustrated in more detail. The screwing module 38 has in this connection a screwing head 39 that is rotatable within a screwing chamber 40 that is loadable with sterile air and is arranged on top of the sterile area S'''. By means of the screwing head 39, the cap 3 that has been placed onto the bottle 2 under sterile conditions az a spacing W (FIG. 17) is gripped after an appropriate lowering movement (arrow N; FIG. 18) has been carried out and, by performing subsequently a turning or screwing movement (arrow K, FIG. 19), is moved about a vertical axis N' so that a tight closure of the cap 3 and the bottle 2 by screw connection is achieved.

The screwing head 39 operating within the screwing chamber 40 is connected to an upper turning and lifting drive 41 that is arranged outside of the housing 16 (FIG. 3). In this way, in contrast to the third sterile area S''' that receives sterile air and is provided for the described screwing phase, it is sufficient to provide in the screwing chamber 40 an air supply fulfilling only ultraclean requirements; in this way, a significant lowering of the technical expenditure is achieved. The two chambers S''' and 40 are connected in the area of the movement gap 42 that can be supplied with sterile air.

The enlarged illustration according to FIG. 17 shows that in the area of the movement gap 42 connecting the sterile area S" and the chamber 40 an annular chamber 44 is provided that is connected to a sterile air supply 43; from the supply 43 the sterile air can be distributed into the screwing chamber 40 as well as into the third sterile area S" (FIG. 17, arrow R, R'). It is understood that by means of sterile air supply 43 also a supply of hydrogen peroxide aerosol is possible wherein the supply action can be carried out in cycles or at predetermined intervals. The flow arrows R" show the action of the exhaust provided in the screwing chamber 40. The screwing head 39 that can be placed onto the caps 3 when standing still is provided in an expedient configuration with a server motor 41 as a drive (FIG. 3).

In the sterile area S" near the rear wall part 16" when viewed in the conveying direction F an additional sterile air supply 46 is provided that generates a protective action relative to the area X' containing ambient air.

In addition to the laminar vertical flow U' through an exhaust gap 47 a flow U is generated so that a recontamination of the sterile area S" is securely prevented.

By means of the sterile housings 14, 15, 16 that are arranged in series relative to the linear machine 1 and form the sterile areas, respectively, a terminal arrangement, viewed in the direction of the conveying device, of the closing device 8 and the screwing module 38 that have movement-intensive modules is provided. In this linear arrangement it is possible to keep the respective chambers substantially sterile by means of vertical flows with minimal expenditure of sterile air. In this optimal control of the sterile conditions in S, S', S" or the entire closure area T the respective vertical walls 14", 25, 31, 45, and 16" between the sterile areas are effective like sluices so that the bottles 2 can be sterilely closed with high productivity.

In a further configuration of the machine 1, not illustrated in detail, it is provided that preferably in place of the modular closing device 8 with the screwing head 39 a welding or gluing device is provided that can be integrated into the method sequence. By doing so, in particular a thermal closure process can be performed such that appropriately configured caps 3 and bottles 2 can be connected by bonding or fusing.

The specification incorporates by reference the entire disclosure of German priority document 10 2005 032 322.7 having a filing date of Jul. 8, 2005.

While specific embodiments of the invention have been shown and described in detail to illustrate the inventive principles, it will be understood that the invention may be embodied otherwise without departing from such principles.

What is claimed is:

1. A method for closing bottles with sterile caps, the method comprising the steps of:
   placing the caps adjacent to one another in a non-sterile environment in a vertical arrangement;
   supplying the caps in a substantially vertical transport direction to a first sterile area, wherein an interior of the caps faces in a horizontal direction;
   sterilizing the caps in the first sterile area while the interior of the caps faces in the horizontal direction;
   transferring the caps from the first sterile area into a second sterile area;
   feeding filled bottles linearly to the second sterile area;
   placing the caps by a placing device onto the bottles to produce a bottle-cap unit in the second sterile area;
   conveying the bottle-cap unit to a third sterile area; and
   subsequently closing the bottle with the cap by a closing device, wherein the closing device is not the placing device.

2. The method according to claim 1, wherein, in the step of subsequently closing the bottle, a relative movement between the cap and the bottle is carried out by a push-and-snap-on action or a screwing action.

3. The method according to claim 1, wherein the caps that have been sorted outside of the first sterile area into vertical areas of the transport path with the interior being horizontally accessible are transported in synchronized fashion into the first sterile area that is to be passed vertically, are sterilized by a horizontal spraying device with a sterilization agent, are guided on a transport stretch determining a residence time of the sterilization agent to a spraying and drying area, are subsequently deflected on the transport path into a turned position such that the interior faces downwardly and are moved in the turned position into the second sterile area and placed onto the bottles.

4. The method according to claim 1, further comprising the step of presterilizing the caps during the step of supplying to the first sterile area by an air-sterilization agent mixture exiting from the first sterile area.

5. The method according to claim 1, wherein the caps when passing the first sterile area are sprayed at least phase-wise with a sterilization agent containing hydrogen peroxide, wherein the sterilization agent is introduced with overpressure into the interior of the caps, and wherein subsequently a drying step is performed by at least blowing out the interior of the caps.

6. The method according to claim 5, wherein in the first sterile area simultaneously several of the caps moveable on the transport path are sterilized and dried.

7. The method according to claim 1, wherein the first sterile area, the second sterile area, and the third sterile area are protected against recontamination by individually generated laminar displacement flows that contain at least one of sterile air and a sterilization agent.

8. The method according to claim 1, further comprising the step of introducing displacement flows of sterile air into a zone between the first and second sterile areas for preventing recontamination of the caps and the filled bottles and for ensuring aseptic closure of the filled bottles.

9. The method according to claim 1, wherein in an area where the caps are placed onto the bottles sterile air is supplied and guided in laminar flow downwardly about the incoming bottles.

10. The method according to claim 1, wherein the bottles are plastic bottles and wherein the plastic bottles and the caps are supplied on several paths in a synchronized fashion into the second sterile area and are transported out of the second sterile area as a bottle-cap unit.

11. A machine for sterile closing of bottles with caps, the machine comprising:
   a sterilization device, defining a first sterile area and comprising an individualization device for picking up caps and a vertical transport path feeding the caps, orientated with an interior of the cans facing in a horizontal direction, in a downward vertical direction from the individualization device to a sterilization chamber of the sterilization device, wherein the sterilization device is adapted to sterilize the caps in the sterilization chamber while the interior of the cans faces in the horizontal direction;
   a linear horizontal bottle supply;
   a placing device receiving the caps from an exit of the sterilization device and placing the caps onto bottles supplied by the linear horizontal bottle supply to the placing device;

a closing device arranged at a distance from the placing device and having at least one closing member for closing the bottles with the cap placed thereon, respectively;

a conveying path extending from the placing device to the closing device and conveying the bottles with the can placed thereon from the placing device to the closing device; and wherein the sterilization device, the placing device, and the closing device are configured as synchronized modules of a linear machine.

12. The machine according to claim 11, wherein the transport path passing vertically through the sterilization chamber has a deflection section, wherein the placing device is arranged in a second sterile area, and wherein the deflection section ends proximal to the placing device.

13. The machine according to claim 12, wherein the sterilization device comprises an aerosol spraying device that has several spray nozzles and is arranged proximal to the transport path, wherein the spray nozzles are directed toward a horizontally accessible interior of the caps, wherein the sterilization device further comprises a drying module downstream of the aerosol spraying device in a transport direction of the caps on the transport path, wherein the drying module flushes the caps with hot and/or cold air, wherein the deflection section of the transport path begins at the drying module and exits from a bottom side of a sterile housing of the sterilization device.

14. The machine according to claim 13, wherein the spray nozzles of the aerosol spraying device have cover parts that widen conically in a direction toward the caps located on the transport path, wherein the cover parts ensure that the interior of the caps is directly sprayed with a 32% hydrogen peroxide aerosol in such a way that overpressure is present.

15. The machine according to claim 13, wherein the spray nozzles are arranged parallel and above one another.

16. The machine according to claim 13, wherein three of the spray nozzle are provided and the drying module has three drying nozzles, wherein downstream of the three spray nozzles in the transport direction of the caps several idle cycles are provided.

17. The machine according to claim 13, wherein exhaust air of the drying module is mixed with a hydrogen peroxide aerosol of the aerosol spraying device and wherein the mixture of the exhaust air and of the hydrogen peroxide aerosol is diverted out of the sterile housing toward the individualization device in a direction counter to the transport direction of the caps through a passage of the transport path.

18. The machine according to claim 13, wherein the sterilization device in proximity of the deflection section of the transport path has a partition extending into the second sterile area of the placing device and substantially horizontally across the bottle supply.

19. The machine according to claim 18, wherein the deflection section of the transport path above the partition opens through an opening in a housing wall of the sterile housing into the second sterile area, wherein the opening acts as a sluice because of flows of sterile air.

20. The machine according to claim 12, further comprising a pendulum holder gripping the caps supplied by the deflection section of the transport individually, wherein the placing device has a vertically moveable placing member, and wherein the pendulum holder interacts with the placing member.

21. The machine according to claim 20, wherein the pendulum holder is pivotable in and counter to a bottle supply direction between the placing member and a vertical wall of the second sterile area, wherein the vertical wall is arranged at an exit side of the second sterile area.

22. The machine according to claim 20, wherein the placing member has a forward cylindrical part having an outer side vertically moveable into a position in front of an outlet of the deflection section in such a way that in an upper release position of the cylinder part a leading cap positioned at the outlet in the deflection section is individually transferred to the pendulum holder, gripped by the placing member and in a subsequent vertical downward movement of the placing member placed onto a bottle, wherein the next cap following the leading cap is retained by the cylinder part in the deflection section.

23. The machine according to claim 22, wherein the cylinder part has a bore supplied with vacuum, wherein the bore opens in an annular surface of an end face of the cylinder part so that the caps are secured by vacuum when the cylinder part is placed onto a top side of the caps, respectively.

24. The machine according to claim 23, wherein the pendulum holder has an L-shaped receiving arm having a short leg and a long leg, wherein the short leg is positionable in a receiving position below the placing member and wherein in the receiving position the caps are individually pushed onto the short leg and the caps are picked up individually by the placing member from the short leg by applying vacuum through the bore, wherein the next cap in the deflection section is retained by a cylinder wall of the cap picked up by the placing member, wherein the receiving arm is pivotable away from the placing member, so that the cap picked up by the placing member is vertically downwardly moveable.

25. The machine according to claim 20, wherein the placing member is adjustable in order to provide different vertical stroke lengths in a direction toward the bottles.

26. The machine according to claim 20, wherein the placing member, after having placed the cap onto the bottle, is linearly moveable toward the bottle to provide a snap-on connection or a positive locking connection of the cap and the bottle.

27. The machine according to claim 12, wherein the closing device of the synchronized linear machine has a screwing module having a screwing head moveable arranged in a third sterile area supplied with sterile air, wherein the screwing head engages the caps placed on the bottles by the placing device and screws the caps onto the bottles, respectively.

28. The machine according to claim 27, wherein the screwing module comprises a screwing chamber and a turning and lifting drive, wherein the screwing head is connected with the screwing chamber to the turning and lifting device and wherein the turning and lifting device is arranged external to the screwing chamber that is suitable for ultraclean operation.

29. The machine according to claim 27, wherein the third sterile area and the screwing chamber are connected to one another in the area of a movement gap supplied with sterile air.

30. The machine according to claim 27, wherein in the area of the movement gap an annular chamber is provided that is connected to a sterile air supply, wherein from the annular chamber the sterile air is distributed to the third sterile area and to the screwing chamber.

31. The machine according to claim 27, wherein the air contained in the third sterile area is removable by suction and wherein a vertical wall between the second and third sterile areas acts in the way of a sluice.

32. The machine according to claim 27, wherein the screwing head has a servo motor as a drive.

33. The machine according to claim 11, wherein the sterilization device, the placing device, and the closing device each have a sterile housing that are arranged in serial connection above the horizontal bottle supply.

34. The machine according to claim 33, further comprising supply nozzles and/or exhaust passages supplying essentially germ-free and/or sterile air or sterilization agent of a venting system to the sterile housings, respectively.

35. The machine according to claim 34, comprising cleaning lines enabling sterilization after an automatic cleaning of areas of the linear machine.

36. The machine according to claim 11, comprising a welding or gluing device for fusing or gluing the caps to the bottles, respectively.

37. The machine according to claim 11, wherein the closing device is a welding device.

* * * * *